United States Patent [19]

Vrana et al.

[11] 3,949,736

[45] Apr. 13, 1976

[54] CIRCUIT FOR AUTOMATICALLY DERIVING AND MEASURING RELATIVE VOLTAGES ASSOCIATED WITH IMPEDANCE COMPONENTS OF A BIOLOGICAL OBJECT

[75] Inventors: Jiri Vrana; Milan Cervencl, both of Prague, Czechoslovakia

[73] Assignee: Vyvojova a provozni zakladna vyzkumnych ustavu, Bechovice, Czechoslovakia

[22] Filed: July 15, 1974

[21] Appl. No.: 488,291

[52] U.S. Cl. ............... 128/2.1 Z; 324/57 R; 324/62
[51] Int. Cl.² ................................ A61B 5/05
[58] Field of Search ............ 128/2.1 Z, 2.1 R; 324/57 R, 62 R

[56] References Cited
UNITED STATES PATENTS

| | | | |
|---|---|---|---|
| 2,184,511 | 12/1939 | Bagno et al. | 128/2.1 Z |
| 3,064,641 | 11/1962 | Manetti et al. | 128/2.1 R |
| 3,084,775 | 8/1962 | Calvert | 324/62 R |
| 3,085,566 | 4/1963 | Tolles | 128/2.1 Z |
| 3,316,896 | 5/1967 | Thomassett | 128/2.1 Z |

OTHER PUBLICATIONS

Geddes, "Measurement of Phys. Events by Elec. Impedance", The Am. J. of Med. Elec., Jan.–Mar. '64, pp. 16–27.

Kaysey et al., "Identification of Conductive Tissue of Heart", Am. J. of Med. Elec., Apr.–Jun. '63, pp. 120–124.

Primary Examiner—William E. Kamm
Assistant Examiner—Lee S. Cohen

[57] ABSTRACT

An apparatus for the automatic measuring of values proportional to impedance components of biological objects, particularly of live tissues, provided with circuitry enabling an automatic and instantaneous recording of two values at the moment the applied voltage reaches a required value.

1 Claim, 2 Drawing Figures

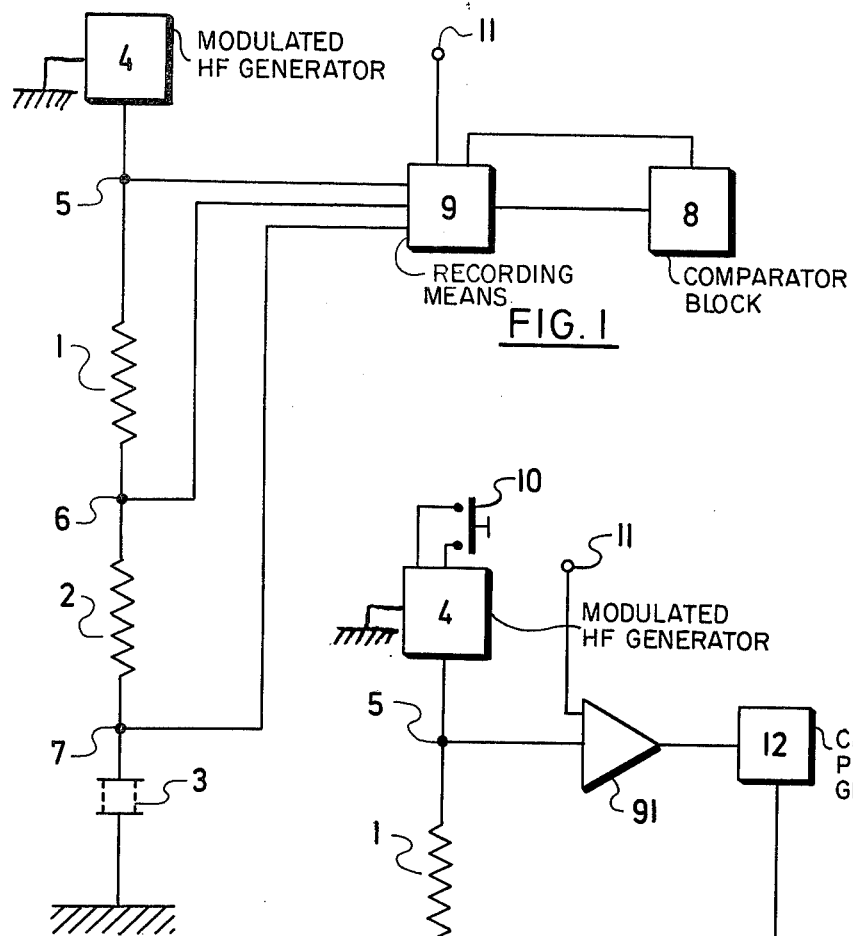
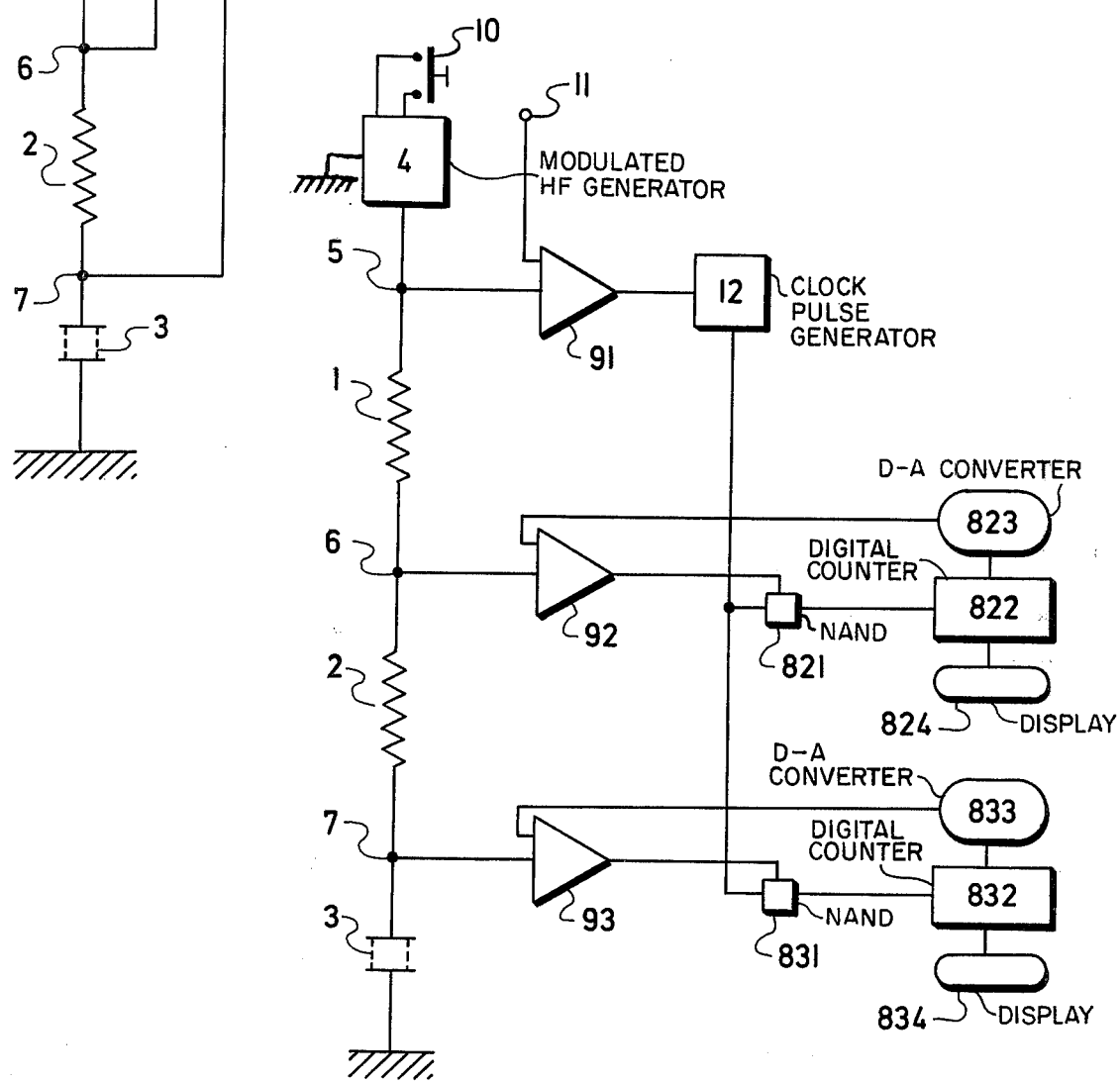

CIRCUIT FOR AUTOMATICALLY DERIVING AND MEASURING RELATIVE VOLTAGES ASSOCIATED WITH IMPEDANCE COMPONENTS OF A BIOLOGICAL OBJECT

This application is related to the co-assigned, co-pending application Ser. No. 488,402, now abandoned, of Vrana and Setka, filed of even date and entitled: "Circuit Arrangement for Determining Changes of Impedance of Biological Objects, Particularly of Tissues," the disclosure of which is incorporated herein by reference in its entirety, and to the co-assigned application Ser. No. 610,422 of Vrana and Setka, filed Sept. 4, 1975.

BACKGROUND OF THE INVENTION

This invention relates to an apparatus for automatically measuring values proportional to impedance components of biological objects, particularly of live tissues, using a high frequency current source connected to a series combination of two equal resistances and of the measured object, which apparatus enables a simultaneous reading to be made of two values at the moment the applied voltage reaches a required value.

A certain impedance of a biological object, as for instance of a live tissue, opposes the passage of an alternating current connected thereto: This impedance has a resistive, a capacitive and an inductive component. The inductive component of live tissues is so small, that it can be neglected from further considerations. The measuring of the resistive and capacitive component of the impedance is accomplished by connecting the investigated live tissue by means of point shaped electrodes together with two equal resistances in series to the terminals of a high frequency current source. The voltage both across the series combination resistance - tissue and across the tissue proper is measured by an electronic voltmeter at a certain level of the supplied high frequency voltage. The obtained voltages are proportional to the required components of the impedance. The absolute values of the components of the impedance can be relatively easily calculated from the measured values, but generally this is not necessary. The measurement is performed at a constant applied voltage and the measured values are sufficiently illustrative for the studies of physiological conditions of the investigated tissue.

A drawback of this process, however, is that the proper measurement must be performed by at least two persons, particularly when investigating tissues of living beings. One person has to take care of the manipulation with the electrodes, the second person attends to the measuring apparatus. The obtained results are, in addition, burdened by a certain error, as at actually used arrangements a simultaneous reading of two different voltages at the moment of an accurate adjustment of the required applied voltage cannot be secured even in the case of the simultaneous use of two measuring apparatus or of one measuring apparatus with the possibility of switching over from one voltage being measured to the other.

SUMMARY OF THE INVENTION

It is an object of this invention to provide an apparatus for automatically measuring values proportional to impedance characteristics of biological objects, where the readings can be automatically registered at the same moment, so that errors due to belated readings of one of the required values are eliminated.

According to this invention, a series combination of two equal resistances and of the investigated object is connected to terminals of a source of an amplitude modulated high frequency current. Parallel to this combination there is connected a block of comparators composed of gate comparators and a control comparator; the gate comparators being directly connected to the recording means by feedback, whereas the control comparator is connected to the gates of the recording means by way of a generator of step-by-step voltage. This interconnection enables the voltages to be registered automatically at the moment when the high frequency voltage connected to the series combination of two equal resistances and the investigated tissue achieves the adjusted level, the voltage both (1) across the series combination resistance - tissue, and (2) across the tissue proper. The simultaneously recorded voltages are registered by a numerical indication or are directly printed on a suitably arranged recording output. The attendance of the measuring arrangement according to this invention is thus limited merely to the pressing of a starting button. The resulting values are not burdened by an error due to belated failure of simultaneous reading.

DESCRIPTION OF DRAWINGS

In the attached drawings:

FIG. 1 illustrates the principle of interconnection of the apparatus according to this invention; and, FIG. 2 illustrates an example of a practical embodiment of such interconnection.

DESCRIPTION OF PREFERRED EMBODIMENT

The series combination of two equal resistors 1, 2 and of the investigated tissue 3, as shown in FIG. 1, is connected across the terminals of an amplitude modulated generator 4, generating high frequency current. A comparison voltage, stabilized to the level $U_1$, is supplied to a terminal 11 of a block of comparators. At the moment when the amplitude of the supplied signal reaches the level $U_1$ at the point 5, the block of comparators 9 which are connected to terminals 6 and 7 at opposite ends of resistor 2, serves the voltages at points 6 and 7. Such voltages are evaluated by a recording means 8 as resulting values $U_2$ and $U_3$, respectively.

FIG. 2 shows a practical wiring diagram of the arrangement of FIG. 1. As recording means numerical units are used, consisting of Nand gates 821 and 831, of counters 822 and 832, of numerical - analog converters 823 and 833, and of numerical indicators 824 and 834. The amplitude modulated generator 4 is started by pressing the button 10, feeding the series combination of two equal resistors 1, 2 and of the investigated tissue 3 with current of a frequency of $10^5$ cycles per second at a current density of the order of $10^{-6}$ A. The comparator 91 compares the amplitude modulated signal from the generator 4 with the voltage on the terminal 11, stabilized to a level $U_1$=4mV. At the moment the amplitude of the modulation achieves the level $U_1$, the auxiliary generator 12 of step-by-step voltage starts to be operated. The comparator 92 simultaneously compares the voltage at point 6 with the output of the numerical-analog converter 823; in case the levels are equal, the comparator 92 locks the gate 821, stopping the counter 822 so that the measured voltage remains recorded on the numerical indicator 824 as the resulting value $U_2$. Similarly, the comparator 93 simultaneously compares the voltage at point 7 with the numerical-analog converter 833; in case the levels are equal, the comparator 93 locks the gate 831, stopping the counter 832 so that the measured voltage remains recorded on the numerical indicator 834 as the resulting value $U_3$. The arrangement need not be prepared for a following measurement. After replacing the tissue 3, it is sufficient to press the button 10 and the new values corresponding to resulting voltages $U_2$ and $U_3$ of the new tissue are simultaneously shown on the numerical indicators 824 and 834.

The apparatus for automatically measuring values, proportional to the impedance of biological objects, is an important complement of arrangements for studying the physiological conditions of live tissues. As has been recently found, changes of impedance are an important biological property of tissues, showing typical morphological conditions of cells, particularly enabling an early diagnosis of some carcinomas.

Although the invention is illustrated and described with reference to one preferred embodiment thereof, it is to be expressly understood that it is in no way limited to the disclosure of such a preferred embodiment, but is capable of numerous modifications within the scope of the appended claims.

What is claimed is:

1. In a circuit for automatically deriving and measuring relative voltages associated with impedance components of a biological object, a source of amplitude-modulated high-frequency current, first and second equal resistances connected in series with the source, means for coupling the biological object to be investigated in series with the first and second resistances, a first comparator having a first input connected to a first connecting point of the source and the first resistance and a second input connected to a reference voltage, a step-by-step voltage generator having a triggering input connected to the output of the first comparator, second and third comparators individually having first inputs connected to a second connecting point of the first and second resistances and to a third connecting point of the second resistance and the coupling means, respectively, first and second means for recording the values of voltages at the second and third connecting points, first and second gate means having outputs individually connected to the inputs of the first and second recording means, respectively the first and second gate means further having first inputs individually connected to the outputs of the second and third comparators, respectively and second inputs connected to the output of the step-by-step voltage generator, and feed-back means for individually coupling the outputs of the first and second recording means to second inputs of the second and third comparators, respectively.

* * * * *